(12) United States Patent
Strnad et al.

(10) Patent No.: US 8,147,530 B2
(45) Date of Patent: Apr. 3, 2012

(54) VARIABLE AXIS LOCKING MECHANISM FOR USE IN ORTHOPEDIC IMPLANTS

(75) Inventors: Lee A. Strnad, Broadview Hts., OH (US); Amanda Martin, Norton, OH (US); Dustin Ducharme, Akron, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 1432 days.

(21) Appl. No.: 11/713,397

(22) Filed: Mar. 2, 2007

(65) Prior Publication Data

US 2007/0212915 A1 Sep. 13, 2007

Related U.S. Application Data

(60) Provisional application No. 60/780,032, filed on Mar. 7, 2006.

(51) Int. Cl.
*A61B 17/80* (2006.01)

(52) U.S. Cl. ........................................................ 606/290

(58) Field of Classification Search .................. 606/280, 606/282, 283, 286–291
See application file for complete search history.

(56) References Cited

U.S. PATENT DOCUMENTS

| | | | |
|---|---|---|---|
| 5,954,722 A | 9/1999 | Bono | |
| 6,030,389 A | 2/2000 | Wagner et al. | |
| 6,235,033 B1 * | 5/2001 | Brace et al. | 606/288 |
| 6,331,179 B1 | 12/2001 | Fried et al. | |
| 6,454,769 B2 | 9/2002 | Wagner et al. | |
| 7,141,051 B2 | 11/2006 | Janowski et al. | |
| 7,175,624 B2 | 2/2007 | Konieczynski et al. | |
| 7,940,913 B2 * | 5/2011 | Patel et al. | 379/265.02 |
| 2002/0058939 A1 | 5/2002 | Wagner et al. | |
| 2004/0068319 A1 * | 4/2004 | Cordaro | 623/17.11 |
| 2004/0127896 A1 * | 7/2004 | Lombardo et al. | 606/61 |
| 2005/0004574 A1 * | 1/2005 | Muckter | 606/69 |
| 2005/0049593 A1 * | 3/2005 | Duong et al. | 606/69 |
| 2005/0143742 A1 | 6/2005 | Porcher | |

* cited by examiner

*Primary Examiner* — Thomas C. Barrett
*Assistant Examiner* — Michael Araj
(74) *Attorney, Agent, or Firm* — Hudak, Shunk & Farine Co. LPA

(57) ABSTRACT

A locking mechanism assembly to allow locking of a fastener in an orthopedic implant having its axis at a variable angle relative to the axis of a concavely rounded through opening in the implant. The assembly includes a convexly rounded ring shaped locking cam insert which mates with the through opening and further which includes an expansion slot. The cam insert includes two cam raceways on the inside that are engaged by cam members on the head of the fastener. The cam members increase radially and expand the insert in the through opening to hold it in position by friction. The cam insert further includes a stop member that inhibits the cam insert from rotating as the fastener is rotated in the cam insert and locks it into the desired position.

3 Claims, 3 Drawing Sheets

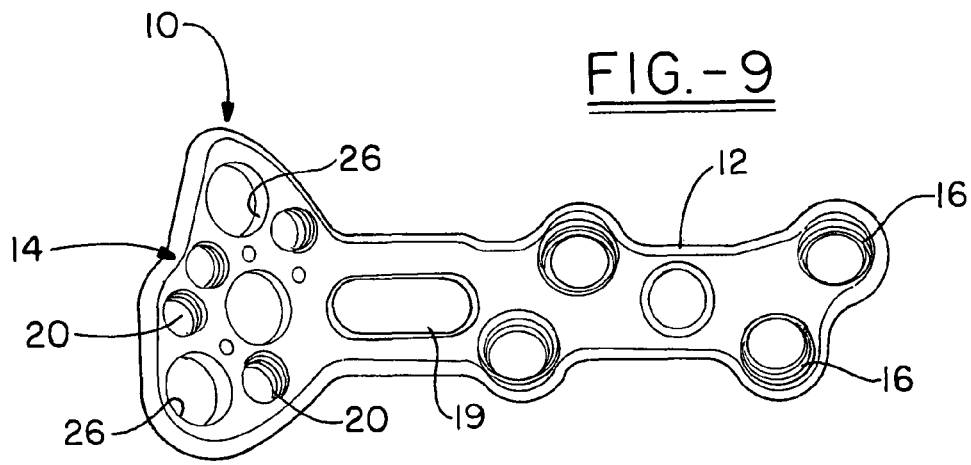
FIG.-9
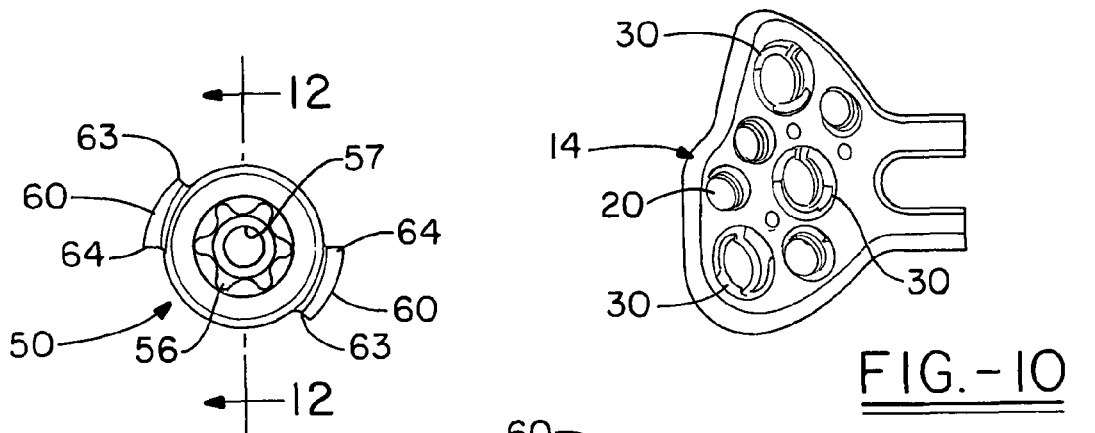
FIG.-11
FIG.-10
FIG.-12
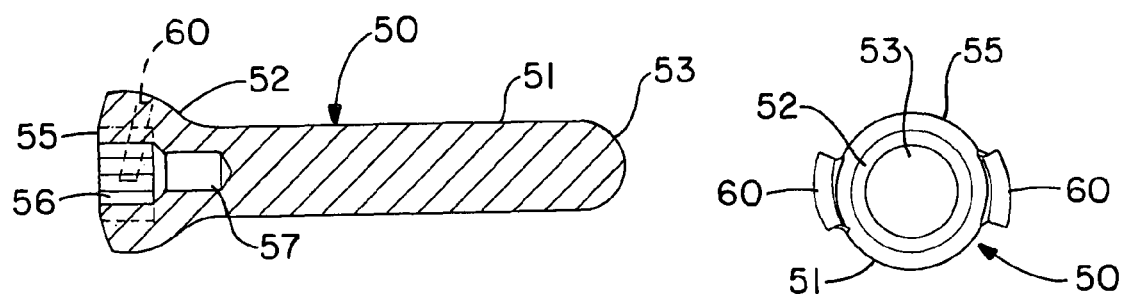
FIG.-13
FIG.-14

VARIABLE AXIS LOCKING MECHANISM FOR USE IN ORTHOPEDIC IMPLANTS

This application is based on U.S. provisional application Ser. No. 60/780,032, filed on Mar. 7, 2006

FIELD OF THE INVENTION

The present invention relates to a mechanism for allowing a screw or peg to be used in an orthopedic implant, such as a plate, at a variable axis and subsequently to be locked into a desired orientation.

BACKGROUND OF THE INVENTION

The field of orthopedics has included countless advances in the design of implants for internal fixation. The present invention provides an advance in the design of an assembly which allows a fixator, including for example, a screw, or peg to be inserted through a stabilizer, such as a plate, anchor or cage, at a variable angle in order to best capture a bone or bone segment with the fixator. The angle can subsequently be locked to fix the bone or bone segment relative to the plate, or to fix the plate relative to the bone or bone segment. The invention allows for at least about 25°, and more preferably 30° of angulation relative to a longitudinal axis of the opening that the fixator is inserted through.

There are numerous applications which can benefit from such a mechanism. Specific examples include use in the small bones, such as the metacarpals and carpals, and the metatarsals and tarsals, although it is understood, that the mechanism can also be of great use in other areas of the body, including the long bones, the pelvis and the spine.

SUMMARY OF THE INVENTION

The assembly of the present invention includes a convexly rounded, and preferably spherical, locking insert that is seated in the concavely rounded, preferably spherical corresponding opening in the implant. The locking insert has an expansion slot and further includes one or more grooves, or cam raceways that receive the wings, or a camming member or more preferably, a plurality of camming members which extend radially outward from the fixator. In particular, the fixator, may be a screw or peg, which includes 2 or more camming members that extends radially outward and partially around the head of the screw or peg, and which increase in the radial dimension. These camming members engage the cam raceways and cause the locking insert to expand radially in the opening in order to cause a friction fit of the locking insert in the opening and to lock the screw or peg at the desired angle.

BRIEF DESCRIPTION OF THE DRAWINGS

FIG. 9 is a top view of a plate including bores which form a part of the variable axis locking mechanism assembly of the present invention;

FIG. 10 is a top view of the head of the plate of FIG. 9 with the locking inserts in position;

FIG. 11 is a top view of the peg of FIG. 8;

FIG. 12 is a cross section of the peg of FIG. 8 taken along line 12-12 in FIG. 11;

FIG. 13 is a cross section of the peg of FIG. 8 rotated radially 90° from the view of FIG. 12;

FIG. 14 is an end view of the peg of FIG. 8;

DETAILED DESCRIPTION OF THE INVENTION

Figure 1:
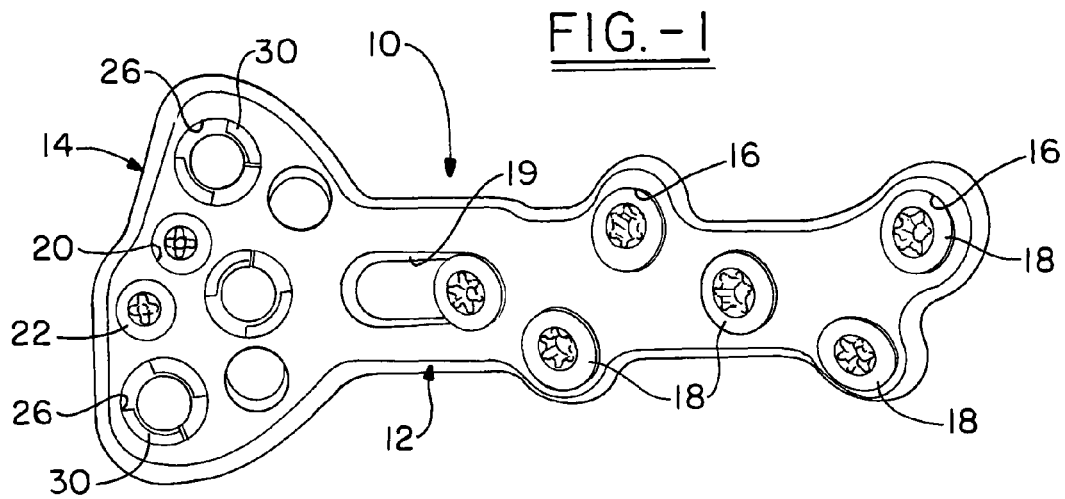
FIG. 1 is a top view of a distal radius plate illustrating an embodiment of the variable axis locking mechanism assembly in accordance with the present invention.
Figure 2:
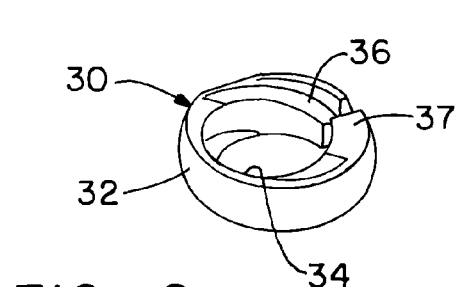
FIG. 2 is a perspective view from the top and the side of a locking insert of the present invention.
Figure 3:
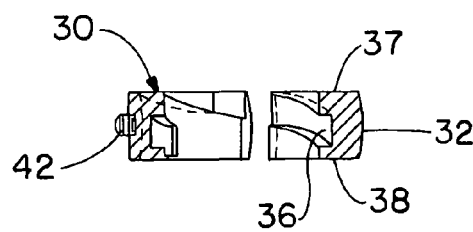
FIG. 3 is a cross section of the locking insert of FIG. 2 taken along line 3-3 of FIG. 6.
Figure 4:
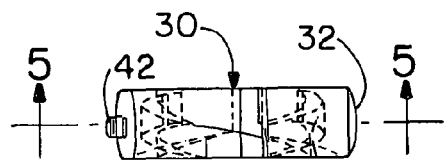
FIG. 4 is a side view of the locking insert of FIG. 2.

FIG. 1 shows a variable axis locking mechanism assembly in the distal head portion of a distal radius plate. The plate 10 has a proximal portion 12 connected to a palm shaped head portion 14. The proximal plate portion includes several holes 16 for screws 18, and a central slot 19. The head 14 includes holes 20 for screws or pegs 22. In particular, there are both fixed angle screws or pegs 24, which can be locking screws which include a threaded head that engages female locking thread in the holes 20 of the plate head. The plate head also includes larger holes 26 that form part of the variable axis locking mechanism of the present invention. These holes 26 are concavely rounded, and preferably partially spherically rounded so that they correspond in shape with the convexly rounded and preferably partially spherically rounded locking cam inserts 30. This allows a rotation of the cam insert 30 in the larger holes of about 30° of conical rotation about a longitudinal axis of the hole 26. The insert as shown in FIGS. 2 through 6, and 15 is a ring shaped insert, having smoothly rounded exterior walls 32, which optionally can include a higher friction surface as is created by knurling, milling or otherwise roughening or texturing the surface. The insert further includes a central opening 34 which has one or more grooves or cam raceways 36. The cam insert 30 has a top surface 37 and a bottom surface 38 which are relatively planar, but include the opening for the cam raceways 36.

Figure 5:
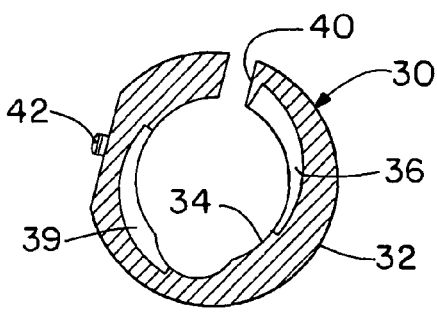
FIG. 5 is a cross section of the locking insert taken along line 5-5 of FIG. 4.
Figure 6:
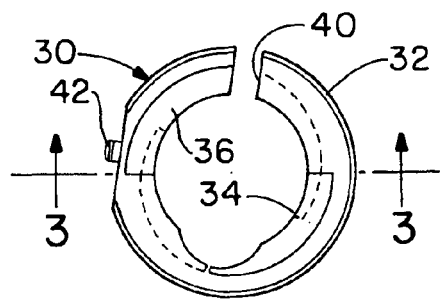
FIG. 6 is a top view of the locking insert of FIG. 2.
Figure 7:
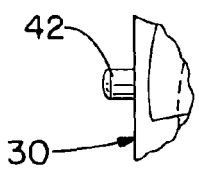
FIG. 7 is a detail of the stop shown in FIG. 6.

Preferably, the cam insert includes 2 cam raceways which begin about 180° from each other and spiral a portion of the way down and around the inside of the cam insert. The cam raceways decrease in the radial dimension from their open starting points on first end as can be seen in FIG. 5. The grooves forming the cam raceways are open, and preferably only for a portion of the top 37 of the insert. This open area of the race allows the cams to be introduced into the race. Subsequently, as the peg is turned in the camming insert, the cam engages the cam race and causes the insert to expand at the gap. This action causes the insert to lock in the recess 26 in the plate which receives the insert.

Figure 15:
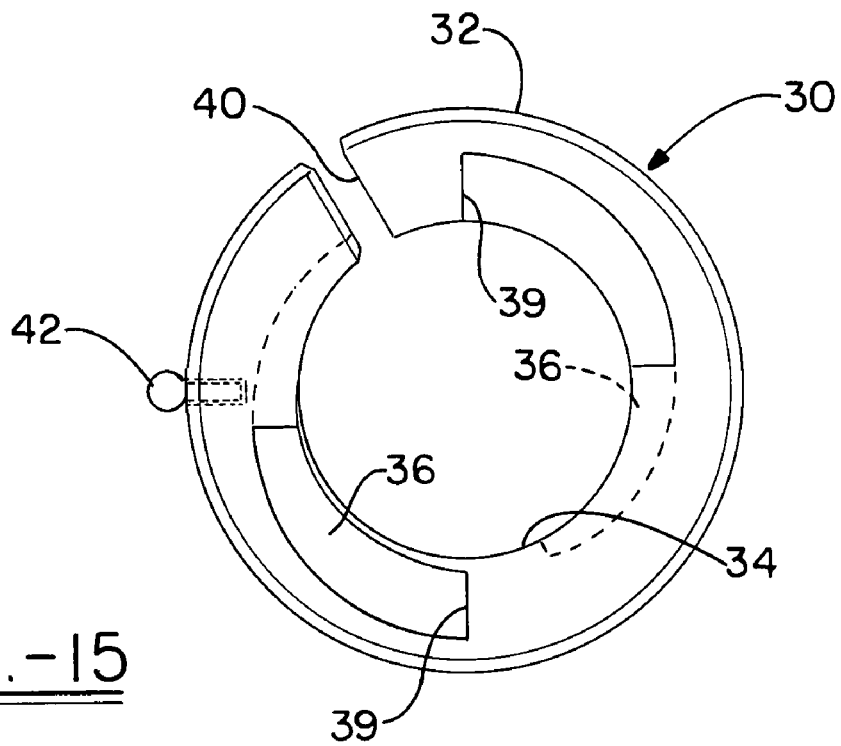
FIG. 15 is a top view of the locking cam insert in the plate and showing the stop recess in phantom.

FIG. 15 illustrates the top openings 39 to the cam raceways 36. Further, the insert 30 has an expansion slot 40 which is essentially a planar slice taken in the insert to create a gap. The gap expands during use to allow the insert to be held in position in the hole by a friction fit. Further, the cam insert 30 includes a stop 42 that resides in a hemispherical well 44 in the hole 26 of the plate. The stop is a projection that is received in the well 44 so as to retain the stop 42 and prohibit the cam insert from turning with the peg as it is turned relative to the plate. This forces the insert to expand the slot 40 to lock it into position.

Figure 8:
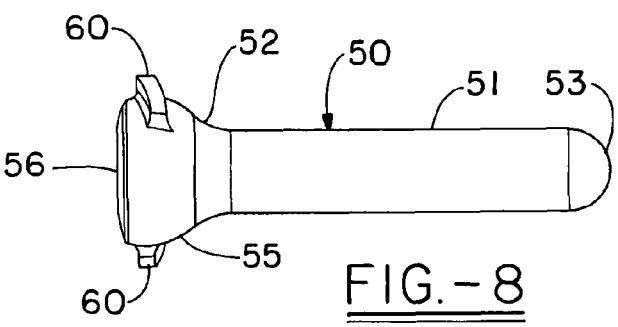
FIG. 8 is a side view of a smooth shaft variable axis locking peg that can be used as part of the locking mechanism assembly of the present invention.

FIG. 8 illustrates a variable axis locking peg 50 that can be used with the locking mechanism of the present invention. In particular, the peg 50 has a smooth shaft 51 with a rounded or blunt insertion tip 53. The shaft is connected by a neck area 52 to a locking head 55 which may include a torque driving recess 56 with a bore 57 to provide for an interference fit with the post of a torque driver so that the peg is self-retained. The head 55 also includes a pair of tapering flanges or wings 60 which act to engage the cam raceways 36 in the cam insert 30 shown in FIGS. 2 through 6. While the camming mechanism is shown as including only two wings, it should be understood that the head could include more wings, and specifically three or four. The wings extend from about 40° to about 50° and spiral slightly from the base 63 of the head upward toward the top surface 64. The base is slightly rounded. In a preferred embodiment, the wings have a quadrilateral cross section as can be seen in FIG. 12.

FIGS. 9 and 10 illustrate the plate 10 without the inserts 30 in place in the larger holes 26, as well as without the fixed axis pegs in the holes 20. FIG. 10 illustrates the same plate head having three locking cam inserts 30 in the larger holes 26 of the head.

Figure 16:
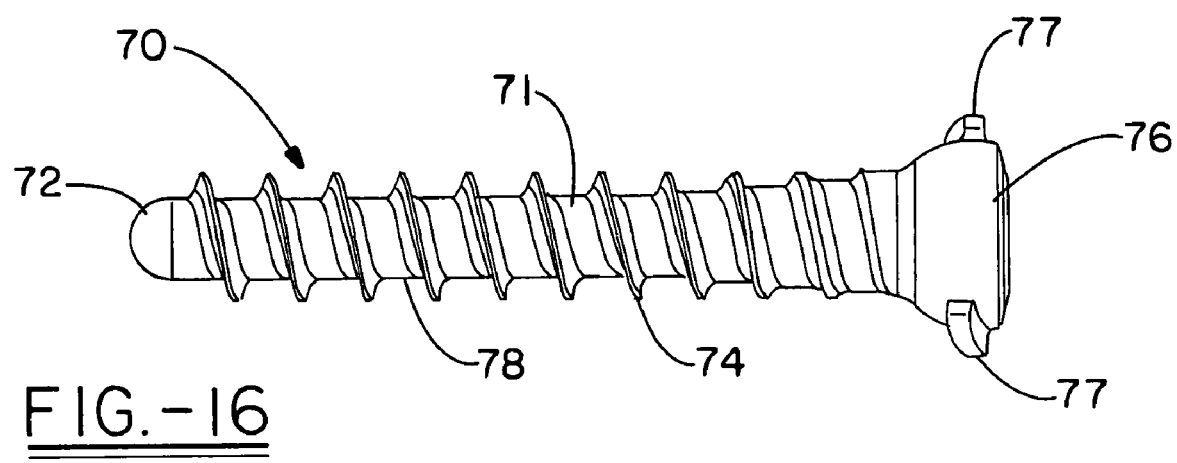
FIG. 16 is a side view of an alternative variable axis locking peg that can be used in the locking mechanism assembly of the present invention.

FIG. 16 shows a variable axis locking screw 70 which is similar to the variable axis locking peg shown in FIGS. 8 and 11 through 14, and has a shaft 71 with a blunt or rounded insertion tip 72. The shaft 71 tapers throughout its length so that the screw 70 does not include a linking neck area as the peg does. The screw does include a locking head 76. The locking head includes a pair of cam wings 77 which are shaped as for the locking peg and which engage the race in the locking insert 30 in the same way as the cam wings of the variable locking peg. The shaft of the variable locking screw 70 is threaded with a thread 74 having a taper to the minor diameter of the shaft while the major diameter 78 does not taper. The head 76 further includes a torque driving recess 79; with an optional bore 80 which retains the screw 70 on the post of a screwdriver.

While in accordance with the patent statutes the best mode and preferred embodiment have been set forth, the scope of the invention is not limited thereto, but rather by the scope of the attached claims.

What is claimed is:

1. A variable angle locking mechanism assembly for use in an orthopedic implant, comprising:
an implant having a through opening having a longitudinal axis and a concavely rounded wall about the longitudinal axis; a ring shaped insert having a central opening with a lateral surface and having a convexly rounded side wall and sized to fit in the through opening in the implant at a plurality of angles relative to the longitudinal axis of the through opening, the side wall including an opening that allows the radial expansion of the insert, the central opening of the insert including at least one raceway in the lateral surface of the central opening and wherein the at least one raceway has a starting point and decreases in the radial dimension from its starting point, the insert further having an expansion slot; and a fastener that is adapted to extend through the through opening and which includes at least one radially extending expansion member which radially increases along a length thereof and which engages the raceway of the insert whereby the expansion member of the fastener can engage the raceway of the insert to selectively lock the insert at an angle in the through opening relative to the longitudinal axis.

2. The variable angle locking mechanism assembly as set forth in claim 1, wherein the fastener has a head which includes an expansion member which has a quadrilateral cross section.

3. The variable locking mechanism assembly as set forth in claim 1 in which the raceways are open, for at least portion of the top of the insert.

\* \* \* \* \*